United States Patent [19]
Kitamura et al.

[11] Patent Number: 5,428,443
[45] Date of Patent: Jun. 27, 1995

[54] LASER DIFFRACTION-TYPE PARTICLE SIZE DISTRIBUTION MEASURING METHOD AND APPARATUS

[75] Inventors: Hiroyuki Kitamura; Yoshiaki Togawa; Juichiro Ukon, all of Miyanohigashi, Japan

[73] Assignee: Horiba, Ltd., Kyoto, Japan

[21] Appl. No.: 134,116

[22] Filed: Oct. 8, 1993

[30] Foreign Application Priority Data

Oct. 11, 1992 [JP] Japan ................. 4-299292

[51] Int. Cl.⁶ ............................................. G01N 15/02
[52] U.S. Cl. ................................. 356/336; 356/338; 356/36
[58] Field of Search .................. 356/335–343, 356/39, 73, 36; 250/574, 576, 222.2; 377/11

[56] References Cited

U.S. PATENT DOCUMENTS

| | | | |
|---|---|---|---|
| 3,879,129 | 4/1975 | Inoue | 356/335 |
| 5,015,094 | 5/1991 | Oka et al. | 356/335 |
| 5,059,395 | 10/1991 | Brittenham et al. | 356/335 |
| 5,305,072 | 4/1994 | Sawada et al. | 356/336 |

FOREIGN PATENT DOCUMENTS 232468 8/1992 Japan .

*Primary Examiner*—Hoa Q. Pham
*Attorney, Agent, or Firm*—Price, Gess & Ubell

[57] ABSTRACT

A particle-size distribution measuring apparatus and method is provided for suspending a sample containing particles in a fluid and introducing the suspended particles into a sample cell. The sample cell is illuminated with light from a laser source and the diffracted light from the particles is measured by an optical detector array. A computer circuit is capable of computing a plurality of graphs of particle-size distribution in repetitive measurement over a predetermined time period. A video display discloses the plurality of graphs in a juxtapositioned arrangement or stacked arrangement to enable the observer to distinguish between any variations in adjacent graphs.

4 Claims, 5 Drawing Sheets

LASER DIFFRACTION-TYPE PARTICLE SIZE DISTRIBUTION MEASURING METHOD AND APPARATUS

BACKGROUND OF THE INVENTION

1. Field of the Invention

The present invention relates to a laser diffraction-type particle size distribution measuring apparatus and method and more particularly, an apparatus and method for determining the stability of the measured results.

2. Description of Related Art

The necessity to measure accurately the size and distribution of particles has become increasingly important in order to determine and evaluate the performance of various powder-type substances across a wide field of applications, such as pharmaceuticals, food stuffs, ceramics, cosmetics, paints, and coloring matters. One form of the apparatus and method utilized to determine particle distribution is a laser diffraction method wherein a powdery sample is disbursed and stirred in a carrier liquid called a dispersion medium to form a suspension. This resulting suspension is then introduced into a measurement flow cell that is then illuminated with laser beams. The detected scattered light from impact with the particles, is measured by an appropriate optical detector array and the results of this measurement are then used to calculate the intensity distribution of the resulting diffracted light and the particle distribution of the sample on the basis of Fraunhofer's diffraction theory and Mie's scattering theory.

Conventionally, the operation of such apparatus has required that the suspension be circulated through a suspension circulating system to reach a uniform condition of suspension so that the flow cell will be appropriately charged with a sample that is representative of the specimen being tested. In order to determine whether the sample has reached a state in which accurate measurements can be made, the suspension is usually circulated through a circulating system after a suitable time period, for example, four or five minutes, after an operation of an ultrasonic vibrator adequately dispersed the particle sample in the dispersion medium. Subsequently, the flow cell is illuminated with laser beams to provide data to create a particle-size distribution graph, for example, of the type shown on the screen in FIG. 4, so that it can be compared with a standard particle-size distribution graph and when there is substantially no difference between them, it can be judged that the suspension is in a stable or measurement condition.

Another method that has been utilized is to again operate the ultrasonic vibrator for a set period of time and then conduct two measurement cycles to obtain two particle-size distribution graphs. These graphs can then be physically compared and when it is decided that there is no significant difference between both particle-size distribution graphs, it is possible to conduct the measurement cycle. As can be appreciated, in the former method it is necessary that a plurality of different kinds of standard particle-size distribution graphs must be prepared and stored so that they can be suitably selected and compared with an obtained particle-size distribution graph. As can be reasonably expected, this may require numerous comparisons until the operator can decide that the suspension of the sample has arrived at a stable condition or measurement condition.

In the latter method mentioned above, it is not required to prepare a plurality of standard particle-size distribution graphs and store them, but it is required to obtain the particle-size distribution graph numerous times until the suspension arrives at a stationary condition and to make individual comparison from the results of each measurement. A printer can print out the results to facilitate such comparisons.

In both operations of a conventional laser diffraction-type particle-size distribution measuring method, the operator involvement can be time consuming and can lead to errors.

As can be appreciated, these problems have occurred not only in those methods wherein the suspension sample is ultrasonically dispersed in a dispersing bath and circulated between the dispersing bath and a flow cell, but also where the suspension is merely stirred in the bath and circulated, and also in the use of a so-called batch method in which the suspension is not circulated and is only ultrasonically dispersed.

The prior art is accordingly looking for an improved method and apparatus for determining the stability and uniform suspension of the particles to enable a measurement cycle.

OBJECTS AND SUMMARY OF THE INVENTION

The present invention provides a particle-size distribution measuring apparatus and method for suspending a sample containing particles in a fluid and introducing the sample into a sample cell. The sample cell is then illuminated with a light, such as laser beams, and the diffracted laser beams or light from the particles are then appropriately measured at positions around the sample cell. The specific particle-size and distribution of particles are then computed and can be provided in the form of a plurality of graphs over a predetermined time period. This graph information can then be visually displayed so that the graphs are juxtapositionedly arranged to enable an observer to distinguish between variations in adjacent graphs. In this regard, a video display can create a simulated three-dimensional display on the screen for particle-size being a first coordinate, distribution percentage or rate being a second coordinate and time being a third coordinate. The observer can then monitor the stacked or progressive array of graphs and determine when the system is stable enough to commence meaningful measurements. Thus, the measurement cycle will start at a point of time when no change is perceived between the stacked series of particle-size distribution graphs and it is assumed that the suspension has arrived at a stationary condition suitable for such measurements.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a laser diffraction-type particle-size distribution measuring method and apparatus with an improved display.

Figure 1:
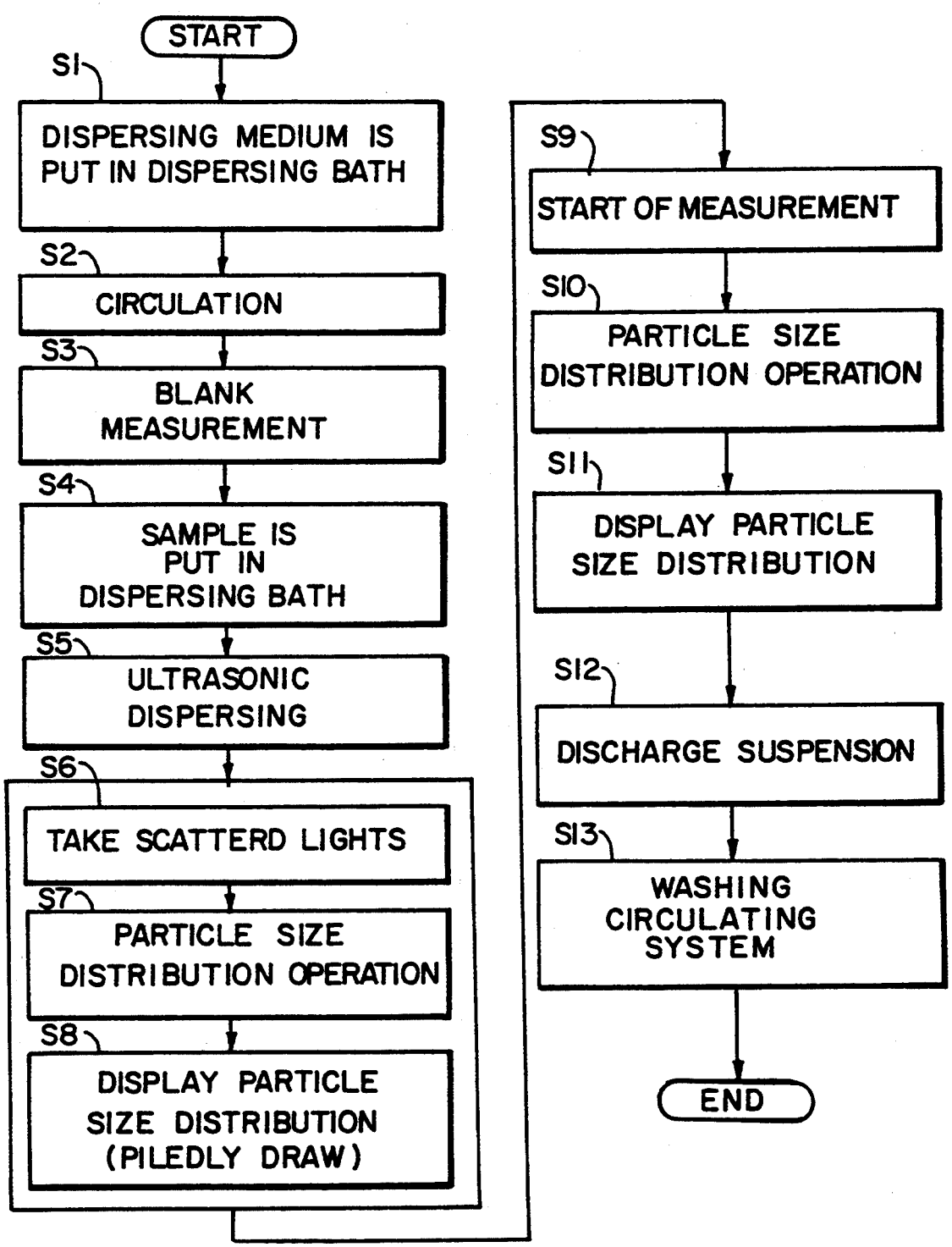
FIG. 1 is a flow chart showing one example of a procedure of a laser diffraction-type particle-size distribution measuring method according to the present invention.
Figure 2:
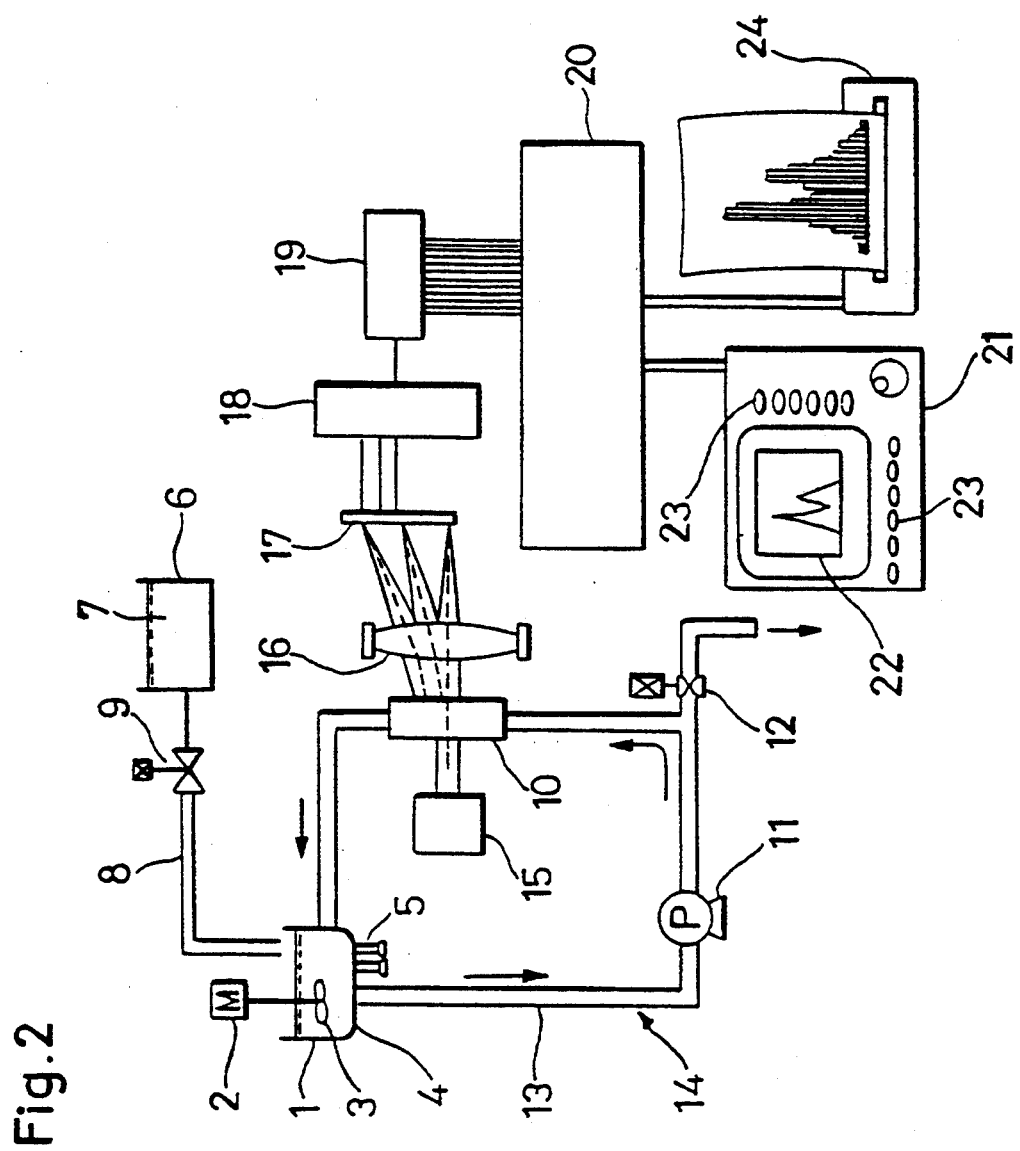
FIG. 2 is a schematic drawing of an apparatus disclosing the structure of a particle-size distribution system.

FIG. 1 is a flow chart showing the operational steps of one example of a laser diffraction-type particle-size distribution measuring method in accordance with the present invention. FIG. 2 is an apparatus that can be utilized the practice the present invention.

Referring to FIG. 2, a dispersing bath or tank 1 can be provided with a stirring blade 3 that is rotated by a motor 2, such as an electrical motor. An ultrasonic vibrator 5 can be positioned at the lower portion of the bath 2 and can be vibrated by a transmitter (not shown) of a conventional configuration that is mounted outside of the bottom surface 4 thereof. A dispersion medium tank housing 6 stores an appropriate dispersion medium 7, a conduit 8 connects the tank 6 with the bath 1 through a closing valve 9, such as an electromagnetic valve, which can be appropriately controlled, for example by automatic computer controls, to release a desired quantity of dispersing medium 7 to the bath 1.

A flow cell 10 acts as the sample cell which can be charged with a suspension of the unknown particle sample and the dispersing medium and it is directly connected with the dispersing bath 1 through a circulating passage or conduit 13 that is also provided with a pump 11 and changeover valve 12. These elements constitute a suspension circulating system 14. A source of a laser light 15 is provided on one side of the flow cell 10 and reference numbers 16 and 17 designate a collecting lens and an optical detector array provided on the other side of the flow cell 10, respectively. As can be readily appreciated, there are various forms of conventional sample cells to effectively collect the laser light as it is dispersed or diffracted by the particles in the sample cell 10. Reference number 18 can provide a signal changeover circuit or a multiplexer circuit for addressing, in a sequential manner, various elements of the array of sensors on the optical detector 17. An A/D circuit 19 can convert the analog signals into digital values for transmission across bus lines to a CPU system 20.

The CPU system 20 can perform various forms of control for the respective parts of the apparatus and can also process the digital signals from the optical detector 17 to particularly calculate particle-size distribution. The particular calculation of particle size and distribution can be accomplished in a known manner with the use of a computer program on the basis of the Fraunhofer diffraction theory and the Mie scattering theory.

A monitor 21 can provide a video screen display with various forms of function keys 23 positioned around the display screen 22. The display screen can be of a conventional CTR configuration and is capable of providing an output of any calculation of the particle-size distribution, for example, in the form of particle-size distribution graphs. A printer 24 can provide a hard copy of any calculation of particle-size distribution.

Figure 3:
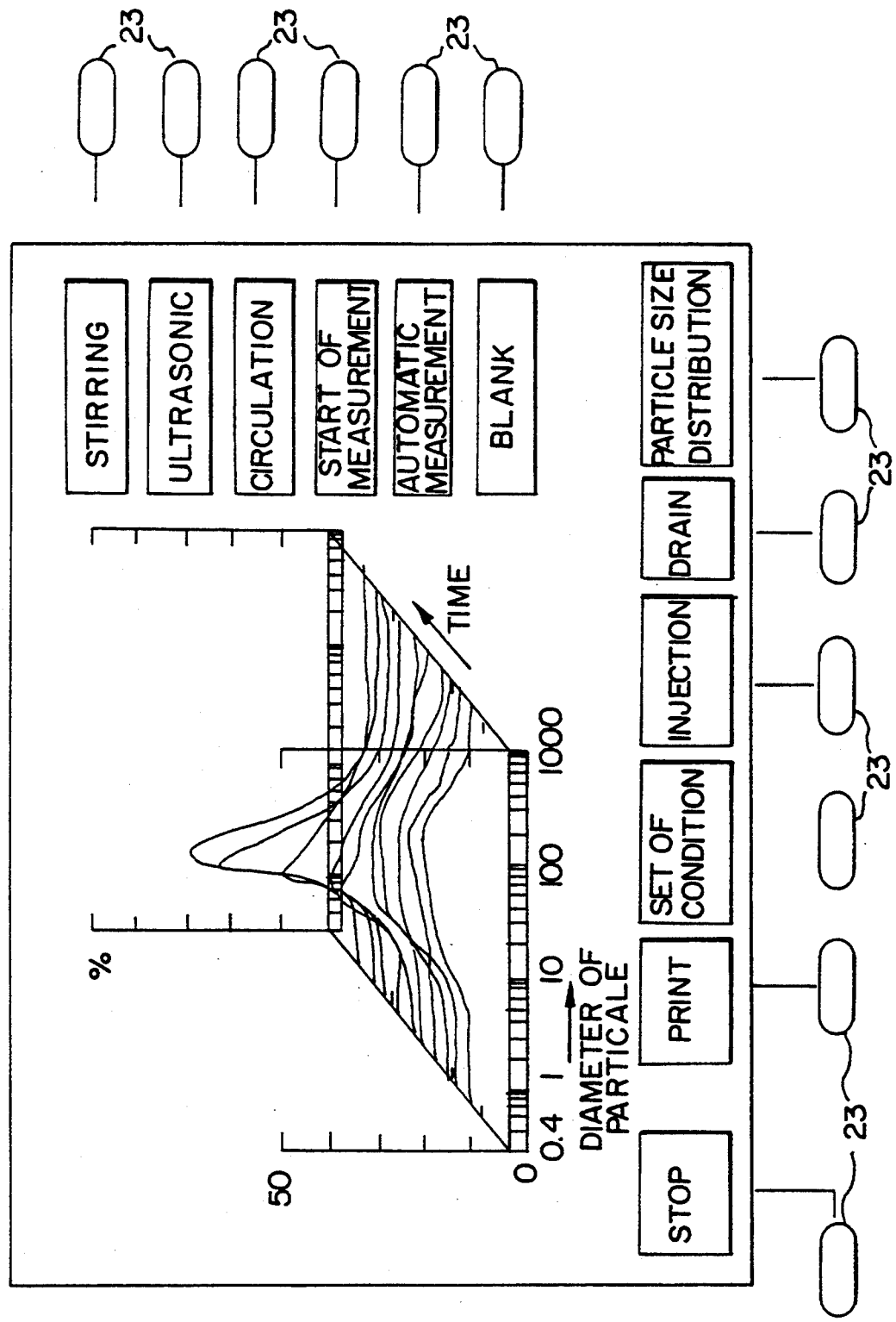
FIG. 3 is a schematic drawing of a display showing a series of particle-size distribution graphs in accordance with the present invention.
Figure 4:
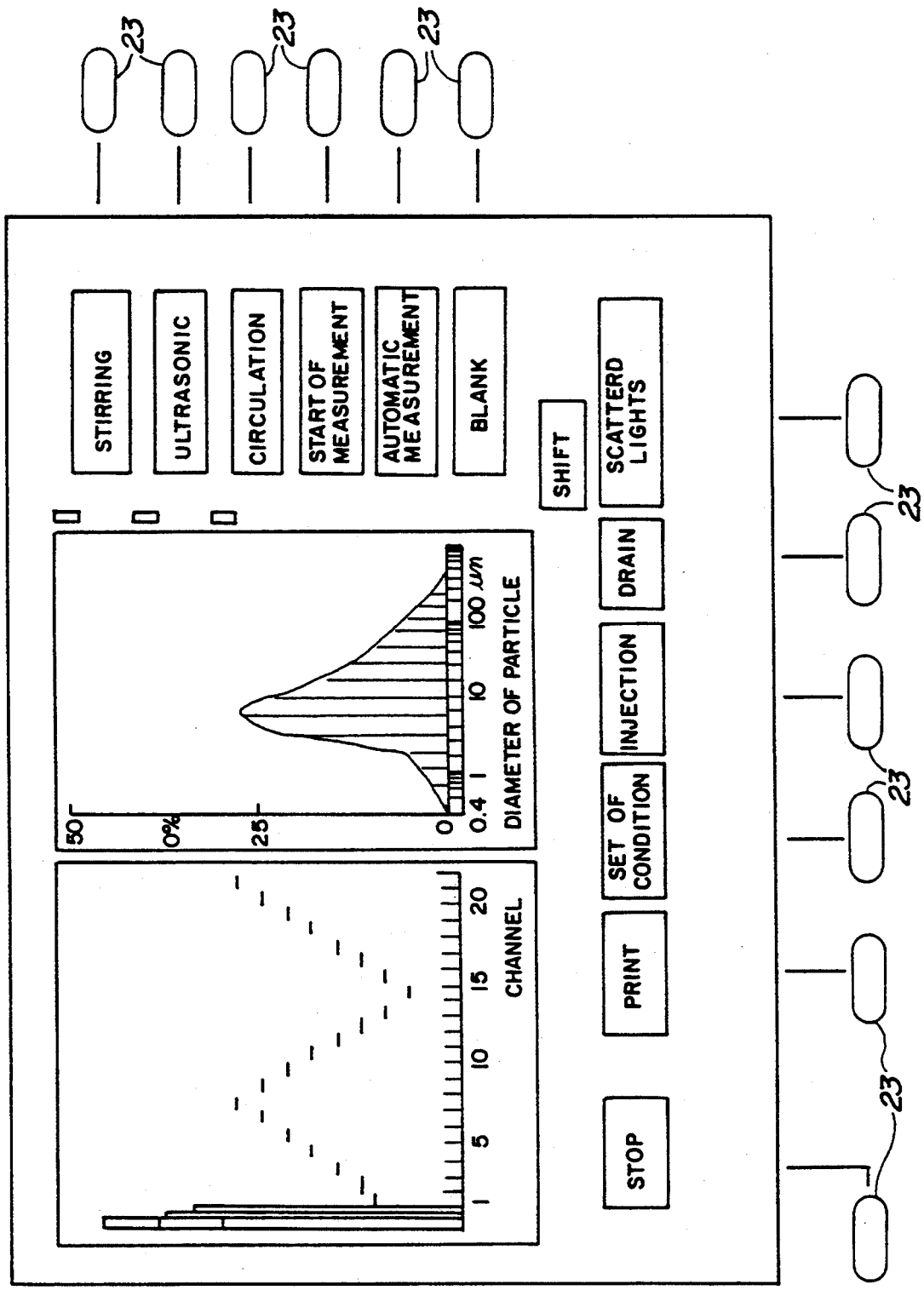
FIG. 4 is a schematic drawing showing a particle-size distribution graph of a conventional method.

Referring to FIG. 3, the view of the monitor 21 having a display screen 22 and functional keys 23 are disclosed in a schematic format. If the injection function key is activated, the closing valve 9 is open to introduce a suitable amount of dispersing medium into the dispersing bath 1. Referring to FIG. 1, a flow chart step S1 is then accomplished. Subsequently, the circulation function key is then activated as step 2 and the stirring pump 11 is operated to circulate the dispersing medium 7, without any sample contained therein, through the circulating system 14 along the circulating passage 13 to thereby fill the sample flow cell 10 with the dispersing medium 7. The blank function key is then operated so that laser beams from the laser light source 15 will be directed through the flow cell to measure the quantity of light scattered or diffracted from the cell under a condition containing no particle sample, e.g., just the dispersion medium. Data obtained at this time can be memorized in the CPU 20 at step 3. After this blank measurement is carried out, a desired amount of sample is then placed into the dispersing bath 1 at step 4. The function key stirring is then operated so that the motor 2 is activated to rotate a stirring blade 3 to stir the dispersing medium 7 containing the sample. Simultaneously with this operation, the ultrasonic function key is also operated so that an ultrasonic vibrator 5 will conduct an ultrasonic dispersement treatment so that the sample may be uniformly dispersed in the dispersing medium 7. With the starting of the ultrasonic dispersing treatment, the circulating function key is operated so that the pump 11 will then circulate the suspension of sample with the fluid medium through the circulating system 14. The circulating system will direct the sample from the dispersing bath 1 through the flow cell 10 and again the flow cell 10 will be illuminated with laser beams and any light scattered or diffracted by the sample will be detected by the optical detector 17 at step S6. A signal corresponding to the intensity of the scattered light is then received from the optical detector 17 through a signal changeover circuit or multiplexer circuit 18 with the analog signals converted by the A/D converter 19 being converted into a digital format and then applied to the CPU 20. This measurement is also stored appropriately in the CPU 20. A particle-size distribution calculation is then conducted, taking into account the data obtained in the initial blank measurement and also the data obtained in the presence of the sample. This step is designated as step S7.

The results of the particle-size distribution operation can then be displayed on the screen 22 of the display operating portion or monitor 21. The operations of steps S6 through step S8 are repeated during the time period when the scattered light that is received by the optical detector 17 is being measured. These operations can then be piledly drawn as a plurality of particle-size distribution graphs juxtapositioned to enable the observer or operator to distinguish between variations in adjacent graphs, as shown in FIG. 3. Thus, the display screen 22 provides a three-dimensional simulation with the particle size being a first coordinate, a distribution rate being a second coordinate, and time being a third coordinate to provide a meaningful display of the information to the operator.

When the suspension arrives at a uniform condition without segregation in the sample cell, that is, a stationary condition, or measurement condition, any change between the particle-size distribution graphs will disappear and a person in charge of the measurement can then judge the point of time when the change between the particle-size distribution graphs disappears as the point of time when meaningful measurements should be taken. In addition, the computer system can be operated so that the particle-size distribution graphs are piledly drawn on the display screen 22 in a cumulative manner, as long as the operation keys are not operated, thus, even if the operator is absent for a period of time, a current final display condition will be maintained in a time sequence to enable a determination of the conditions associated with error-free measurement.

At a particular time, when it appears from the operator's review that the suspension arrives at a stationary condition, a function key disclosed as "start of measurement" is activated at step S9. At that point, the desired measurement is conducted. As can be appreciated, the measurement cycle is again repeated with the scattered light received in the optical detector 17 from the application of laser beams and a conversion of the signals into data of measurement for application to the CPU 20 is initiated. The particle-size distribution operation is then conducted in accordance with known equations to obtain a desired measurement result, see step S10. The desired particle-size distribution results then can be-displayed at step S11. After the desired measurement, the function key "drain" is operated and thereby the closing valve 12 can be opened to discharge all the suspension within the circulating system in accordance with step S12. Finally, the circulating system 14 is supplied with a washing liquid from a washing liquid tank (not shown) to circulate the washing liquid which can also be exhausted from the system at the termination of step S13.

Figure 5:
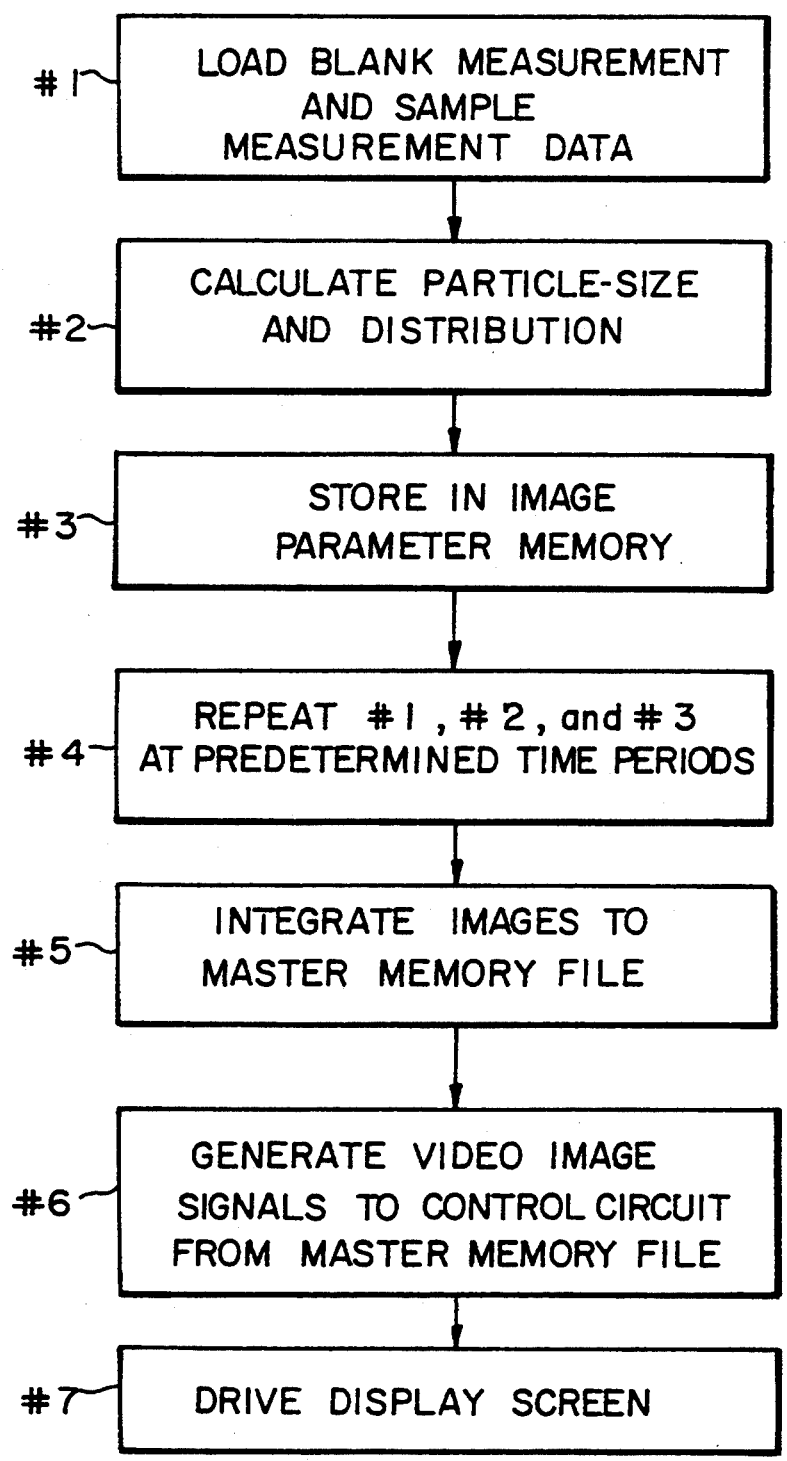
FIG. 5 is a schematic flow chart of providing the stacked graph display.

As can be seen from FIG. 5, a schematic of the display routine of the composite graphs is shown. In step 1, the CPU can load the blank measurement and sample measurement data. In step 2, it calculates particle size and distribution utilizing known equations. In step 3, it stores in an image parameter memory the information supporting the display of a graph of the particle size and distribution. In step 4, it repeats the above steps 1, 2, and 3 at predetermined time periods based upon the completion of repetitive sample measurement data. At step 5, it integrates the information stored in the image parameter memory for each sample measurement data relative to a set time period and integrates the images to a master memory file, which can be refreshed by new sample measurement data. In step 6, it generates video image signals to a control circuit from the master memory file, and at step 7, the control circuit can then use the video image signal to drive the display screen to display the composite or piled series of graphs in a simulated three-dimensional configuration, as shown in FIG. 3.

Although the suspension was ultrasonically dispersed in the dispersing bath 1 and circulated between the dispersing bath 1 and the flow cell 10 in the above-described preferred embodiment, the present invention is not limited by this particular operation and can be applied to other methods wherein the suspension is merely stirred in the bath 1 and circulated and also the so-called batch method in which the suspension is not circulated and is only ultrasonically dispersed.

As can be easily determined, the present invention provides the capacity of an efficient use of operator time with multiple measurement steps that are graphically displayed to enable the operator to verify the measurement system and the optimum time of making measurements. The operator need not be highly skilled to perform this operation, while maintaining a high degree of confidence in the test results.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.,

What is claimed is:

1. A particle size distribution measuring apparatus comprising:
    means for suspending a sample containing particles in a fluid;
    a sample cell;
    means for inserting the suspended particles; into the sample cell;
    means for agitating the suspended particles to the sample cell to provide a uniform dispersion of particles;
    determining means to determine when the suspended particles are uniformly dispersed, including:
      means for illuminating the sample cell with a light;
      means for measuring the light diffracted by the particles;
      means for computing a plurality of graphs of particle size and distribution over a predetermined time period of the same sample; and
      means for displaying the plurality of graphs in a juxtapositioned arrangement to enable an observer to distinguish between variations in adjacent graphs, and
    means for measuring the particle size distribution after the observer determines the suspended particles are uniformly dispersed from the adjacent graphs.

2. The invention of claim 1 wherein the means for displaying includes a simulated three-dimensional display with particle size being a first coordinate, distribution rate being a second coordinate, and time being a third coordinate.

3. A method of determining particle size distribution of a sample comprising the steps of:
    suspending a sample containing particles in a fluid;
    introducing the sample into a sample cell;
    determining that the particles are uniformly dispersed to permit measurement of the sample, including:
      illuminating the sample cell with light;
      measuring the light diffracted by the particles;
      calculating the size and density of particles for a plurality of measurements over a period of time of the same sample; and
      displaying the size, density, and time as graphs in a three-coordinate system so that a plurality of measurement graphs are stacked in a progressive array per unit of time, and
    measuring the size and density of particles in the sample.

4. A particle size distribution measuring apparatus comprising:

means for suspending a sample containing particles in a fluid;

a sample cell;

means for inserting the suspended particles into the sample cell;

means for agitating the suspended particles in the sample cell to provide a uniform dispersion of particles which remains constant for a sufficient period of time to conduct a dependable measurement;

means for monitoring the state of the dispersion of particles to determine when they become uniformly dispersed, including:

means for illuminating the sample cell with a light, means for repetitively measuring the light diffracted by the particles, and means for computing a plurality of graphs of particle size and distribution over a predetermined time period of the same sample;

means for displaying the size, density, and time as graphs in a three-coordinate system so that a plurality of measurement graphs are stacked in a progressive array per unit of the time; and means for measuring the particle size distribution after the plurality of measurement graphs has reached a predetermined minimal variance in shape.

* * * * *